United States Patent [19]

Jach et al.

[11] Patent Number: 5,280,176
[45] Date of Patent: Jan. 18, 1994

[54] X-RAY PHOTOELECTRON EMISSION SPECTROMETRY SYSTEM

[75] Inventors: Terrence J. Jach, Washington, D.C.; Stephen M. Thurgate, Kardinya, Australia

[73] Assignee: The United States of America as represented by the Secretary of Commerce, Washington, D.C.

[21] Appl. No.: 972,854

[22] Filed: Nov. 6, 1992

[51] Int. Cl.⁵ .................................. H01J 37/285
[52] U.S. Cl. ........................... 250/305; 250/306
[58] Field of Search ........................... 250/305, 306

[56] References Cited

U.S. PATENT DOCUMENTS

| | | | |
|---|---|---|---|
| 2,843,750 | 7/1958 | Hillier | 378/83 |
| 3,418,466 | 12/1968 | Herglotz | 378/83 |
| 4,169,228 | 9/1979 | Briska et al. | |
| 4,263,510 | 4/1981 | Cicarelli et al. | |
| 4,417,355 | 11/1983 | Anisovich et al. | 378/49 |
| 4,592,082 | 5/1986 | Pawloski | 378/75 |
| 4,884,290 | 11/1989 | Tamura et al. | 378/83 |
| 5,008,910 | 4/1991 | Van Egeraat | 378/84 |
| 5,138,158 | 8/1992 | Ninomiya et al. | 250/305 |
| 5,144,134 | 9/1992 | Onodera et al. | 250/305 |

FOREIGN PATENT DOCUMENTS 1257482 9/1986 U.S.S.R. .

OTHER PUBLICATIONS

Parratt, "Surface Studies of Solids by Total Reflection of X-Rays", *Physical Review*, vol. 95, No. 2, Jul. 15, 1954, pp. 359–369.

Henke, "Ultrasoft-X-Ray Reflection, Refraction, and Production of Photoelectrons (100–1000-eV Region)", *Phys. Rev. A.*, vol. 6, No. 1, American Institute of Physics, Jul. 1972, pp. 94–104.

Mehta et al., "Enhancement of Surface-Atom Intensities in X-Ray Photoelectron Spectra at Low X-Ray Incidence Angles", *Phys. Lett.* vol. 55A, No. 1, Nov. 3, 1975, pp. 59–61.

Citrin et al., "Surface-atom x-ray photoemission from clean metals: Cu, Ag, and Au", *Physical Review B*, vol. 27, No. 6, Mar. 15, 1983, pp. 3160–3175.

Kruglov et al., "Influence of total external reflection of x rays on the yield of secondary radiations", *Sov. Phys. Solid State*, vol. 28, No. 8, Aug. 1986, pp. 1436–1437.

N. E. Erickson et al., "Characterization of the Imaging Properties of a Double-pass Cylindrical-mirror Analyzer", *Surface and Interface Analysis*, vol. 9, pp. 111–117, (1986).

S. Tougaard, Surface and Interface Analysis, vol. 11, pp. 453–472, (1988).

Kawai et al., "A numerical simulation of total reflection X-ray photoelectron spectroscopy (TRXPS)", *Spectrochimica Acta.*, vol. 47B, No. 8, pp. 983–991 (1992).

*Primary Examiner*—Jack I. Berman
*Attorney, Agent, or Firm*—Marvin S. Towsend

[57] ABSTRACT

A system is disclosed for performing x-ray photoelectron emission analysis which uses a collimated x-ray beam directed to an optically polished sample at a small grazing angle of incidence, a fixed sample/electron spectrometer geometry, and an x-ray detector for detecting x-rays reflected off of the sample. With the system, an enhancement of the x-ray field at layer interfaces in a multilayer sample can take place. The system permits depth profiling of an over layer on a substrate, such as a metal or metal oxide on a metal substrate. The enhancement permits absolute calibration of depth-dependence. The system reduces lineshape distortions due to inelastic electron scattering of exiting photoelectrons and eliminates energy distortions due to changes in the sample position relative to the focal point of the electron spectrometer.

32 Claims, 8 Drawing Sheets

X-RAY PHOTOELECTRON EMISSION SPECTROMETRY SYSTEM

TECHNICAL FIELD OF THE INVENTION

The present invention relates to the field of x-ray photoelectron emission spectrometry, and more particularly to an apparatus and method of x-ray photoelectron emission spectrometry using an x-ray beam directed to the surface of a sample at a small incidence angle.

BACKGROUND OF THE INVENTION

X-ray photoelectron emission spectrometry, also known as x-ray photoemission spectrometry (XPS), is a well-established technique for the analysis of the chemical states of elements found near the surface of a material. In particular, the shift in the binding energy of electrons of various atoms according to their chemical state forms the basis of electron spectroscopy for chemical analysis (ESCA). In ESCA methods employing x-ray photoemission spectrometry, an x-ray source of known photon energy is used to excite photoelectrons in a sample, and the energy distribution of the excited electrons is determined by an electron spectrometer. The difference in energy, after correction for the work function of the spectrometer, is the binding energy of those electrons.

As ESCA methods employing x-ray photoemission spectrometry have been applied to surface and interface layers of increasing chemical and structural complexity, several factors have become evident. The shape of the lines in the photoemission energy spectrum must often be analyzed since the chemical states of a specific element or elements may be too similar in binding energy for their photoemission lines to be completely resolved.

It is also frequently desirable to determine the concentrations of a specific element in different chemical states at different depths in the sample. In this respect, the photoemission yield is inherently attenuated with depth below the surface. It would be desirable, therefore, to enhance the photoelectron emission from elements which may be buried beneath the surface, particularly in a material consisting of thin film layers.

There are several known approaches for carrying out ESCA methods employing x-ray photoemission for obtaining depth-dependence. Previous ESCA methods employing x-ray photoemission have made use of the principles of grazing angle incidence of the exciting x-rays or grazing angle takeoff of the emitted photoelectrons. With decreasing angles of incidence, the penetration depth of x-rays into a surface is likewise decreased, since slight increases in depth require traversing ever longer attenuating paths to reach a specified depth. Within a specific grazing angle of incidence known as the critical angle, $\phi_c$, x-rays are known to be abruptly reflected from a surface, a process known as total external reflection. This reflection is accompanied by an even stronger decay of the x-ray field with depth into the sample. If the angular acceptance of photoelectrons emitted by the material is similarly limited to increasingly grazing exit angles, the depth of the emitting atoms is limited by the increasing attenuation which their photoelectrons will necessarily incur on their path out. By comparing the changes in the x-ray photoemission signal of a specific element as the angle of incidence of the x-rays or the takeoff angle of the photoelectrons is varied, some idea of the depth distribution of the emitting atom species may be obtained.

Some known ESCA methods employing grazing angle x-ray photoemission spectrometry measurements utilize the rotation of a sample with respect to a fixed x-ray source and a fixed electron spectrometer. The rotation of the sample brings about a change in grazing incidence angle and also brings about a change of alignment of the sample with respect to the electron spectrometer, an effect which can result in a distortion of the photoemission lineshape in the energy spectrum of the electrons. Furthermore, all cases of photoemission in which the sampling depth is determined by the mean free path of escaping electrons necessarily results in a photoemission line which is distorted by inelastic energy losses. These distortions can be especially important in the case where the photoemission lines of several chemical species overlap.

Another prior art ESCA method to obtain depth dependence employing x-ray photoemission spectrometry uses a fixed, collimated x-ray beam that is directed to a fixed sample at a specified angle. The photoemission electrons accepted by the electron spectrometer are limited to those leaving the sample at a specific angle, which may be varied When the electron spectrometer is positioned to accept electrons which escape the sample with a large angle relative to the surface, they may originate from a certain range of depths without being significantly attenuated. When the electron spectrometer is positioned to accept only electrons which escape at a very small angle relative to the surface, the range of depths from which they originate is much smaller, since the escape path involves traversing a greater length of material at a given depth. In this example, the escape angle of the electrons may be determined by actual motion of the electron spectrometer relative to the sample or by the motion of an admitting slit between the sample and an electron spectrometer which accepts electrons over a range of angles.

However, distortions in electron spectrometry occur with this method due to changes of electron transport characteristics in the sample and in the electron energy analyzer at different electron escape angles.

Aside from its use in x-ray photoemission spectrometry, the variable grazing incidence angle technique has also been utilized in prior art which sought to obtain elemental analysis with depth dependence by collecting the x-ray fluorescence radiation of atoms which were excited by a collimated x-ray beam. In that case however, the energy resolution of fluorescent radiation is insufficient to obtain the chemical state of the atoms, and attention to the relative alignment of the detector and the sample is not of significance.

It is only in the case of x-ray photoemission spectrometry, where the relative analysis may involve chemical species which differ from each other by energies of the order of less than 2 electron volts (eV), that attention to the lineshape and the distortions which may occur to it are of some consequence.

All of the prior art ESCA methods employing x-ray photoemission spectrometry described above employ apparatus elements in which the position of the sample surface that is exposed to the x-ray beam is varied with respect to the electron analyzer during the course of the analysis And this variation in the position of the sample surface that is exposed to the x-ray beam and the electron analyzer is a cause of distortion in the emitted electron spectrum.

SUMMARY OF THE INVENTION

Accordingly, it is an object of the present invention to provide an x-ray photoelectron emission apparatus that precludes distortions of x-ray photoelectron emission spectra caused by either a rotating sample, a movable electron spectrometer, or a movable entrance slit between them.

Another object of the invention is to provide an x-ray photoelectron emission method that permits determination of thin layer thickness in multilayer samples.

Another object is to provide an x-ray photoelectron emission apparatus and method that enhances the photoelectron emission from elements which may be buried beneath the surface of a multilayer sample, particularly a sample consisting of thin film layers.

Additional objects, advantages, and novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved x-ray photoelectron emission analyzer apparatus is provided. The improved apparatus includes an x-ray source and means for collimating x-rays from the source to provide a collimated x-ray beam. The collimated x-ray beam interacts with a sample within an evacuated chamber. Means are provided for adjusting the collimated x-ray beam to permit the collimated x-ray beam to interact with the sample with an adjustable grazing incidence angle. An electron detector, which is maintained in a predetermined, fixed orientation with respect to the sample, is provided for detecting photoelectron emission from the sample when the collimated x-ray beam interacts with the sample. Means are provided to support the sample in a predetermined, fixed orientation with respect to the electron detector. In addition, means are provided for monitoring the grazing angle of incidence of the collimated x-ray beam that interacts with the sample.

Preferably, the grazing angle of incidence is in a range of 0.1 to 100 degrees. More specifically, means for adjusting the grazing angle of incidence includes means by which the angle of incidence of the collimated beam from the x-ray source can be changed without changing the point of illumination on the sample or the distance between the source and the sample. Also, preferably, the collimated x-ray beam has an energy range from 100 electron volts to 10,000 electron volts. Preferably, the electron detector includes means for providing a record of energy distribution of the detected photoelectron emission from the sample and may, for example, be a cylindrical mirror analyzer or a hemispherical analyzer or a 127° sector analyzer. More specifically, preferably the electron detector includes means for determining the kinetic energy of electrons photoemitted. In this respect, the electron detector includes means for determining the number of electrons of a specified kinetic energy photoemitted by the sample. Preferably, the sample is optically flat and polished; and the means for monitoring the grazing angle of the collimated x-ray beam can be an x-ray detector which detects x-rays reflected off of the sample. The x-ray detector can be an area detector such as a micro-channel plate.

Generally, in accordance with the apparatus of invention, the angle at which the x-rays strike the sample can be varied by moving the x-ray source without changing the relationship of the sample to the electron analyzer. Photoelectrons emitted from near-surface atoms with characteristic energies are measured with the electron spectrometer for different grazing incidence angles of the source beam. The variation in the incidence angle allows selective excitation by discriminating between slightly differing critical angles of different material layers in a multilayer sample as well as enhancement of the x-ray field at interfaces between adjoining layers. This can also be used to determine the depth distribution of particular elements in the sample. The x-ray detector permits the sample to be accurately aligned with the x-ray source, allows the determination of the reflection angle of x-rays from the sample, and measures the intensity of the reflection.

In accordance with another aspect of the invention, a method is provided for analyzing a multilayer sample to determine the respective depths of the respective layers. More specifically, the multilayer sample can have a first layer and a second layer, wherein the first layer is a top layer and has a first-layer critical angle, and the second layer is a substrate and has a second-layer critical angle.

For a two-layer sample, the method of the invention includes the following steps. The sample is supported in a evacuated chamber with a predetermined, fixed orientation with respect to an energy analyzing electron detector. A collimated x-ray beam is directed to the sample at a specified grazing angle of incidence with respect to the sample. The incidence angle of the collimated x-ray beam is monitored by detecting x-rays reflected off of the sample with an x-ray detector, and data are generated which represent the incident angle. The incidence angle is controlled with respect to the sample such that it can be maintained at an angle between the first-layer critical angle and the second-layer critical angle, whereby photoelectron emission intensity from the first layer and the interface between the first and the second layer are enhanced. Photoelectron emission from the sample is detected with the energy analyzing electron detector, and data are generated which represent an energy distribution of the detected photoelectron emission. The data representing the photoelectron energy distribution are evaluated to determine peaks in emission from the different chemical species of the different layers. A determination of the thickness of the first layer is based on a comparison of the detected signals from the two layers at several angles of incidence.

Preferably, the grazing angle is controlled to be an angle greater than the first-layer critical angle and less than the second-layer critical angle; and the sample has an optically polished first layer.

A sample may have a third layer, where the third layer is a substrate; and a second layer both underlies the first layer and overlies the substrate layer. The third layer has a third-layer critical angle; and the incidence angle is controlled to be a grazing angle that is greater than the second-layer critical angle and less than the third-layer critical angle, whereby photoelectron emission intensity from the second layer and the interface between the second and third layer are enhanced. Then the thickness of the second layer can be determined based on detected signals from the second and third layers at several angles of incidence.

Even more generally, the method of the invention can be used with a sample that includes an "n"th layer that underlies an "n-1"th layer. The "n"th layer has an "n"th-layer critical angle; and the "n-1"th layer has an "n-1"th critical angle. The incidence angle is controlled at a grazing angle greater than the "n-1"th-layer critical angle and less than the "n"th-layer critical angle, whereby photoelectron emission intensity from the "n-1"th layer and the interface between the "n-1"th layer and the "n"th layer are enhanced. Then, the thickness of the "n-1"th layer can be determined based on the relative intensity of photoelectron emission peaks with different energies originating from the "n"th and "n-1"th layers as the angle of incidence is varied.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE PREFERRED EMBODIMENTS

Figure 1:
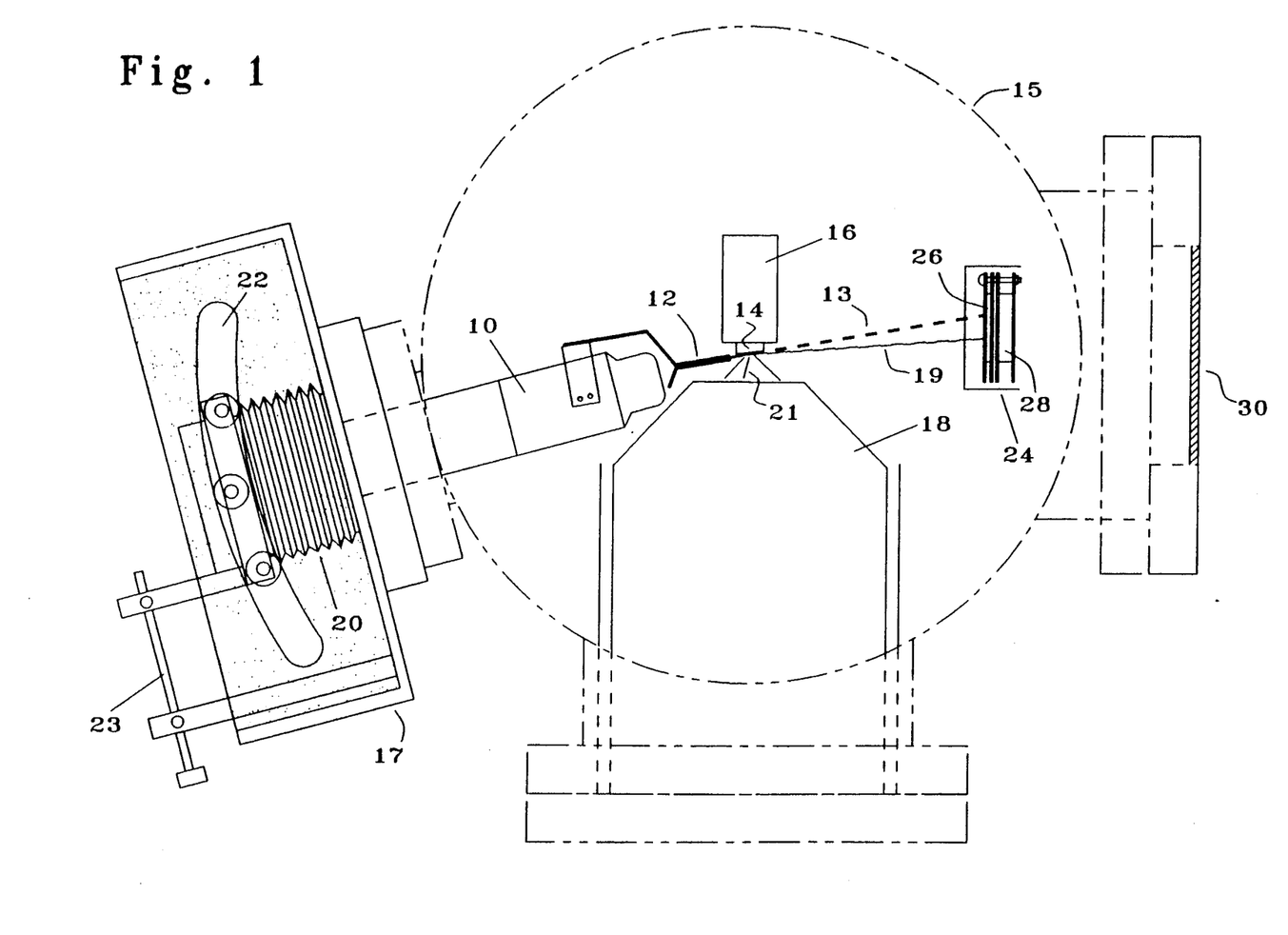
FIG. 1 shows an embodiment of an apparatus of the invention in which an x-ray tube serves as an x-ray source, a microchannel plate with a phosphor screen serves as an x-ray area detector, and a cylindrical mirror analyzer serves as an electron spectrometer; in this embodiment, the grazing angle of incidence of the collimated x-ray beam on the sample is controlled by moving the x-ray source along a circular track.
Figure 2:
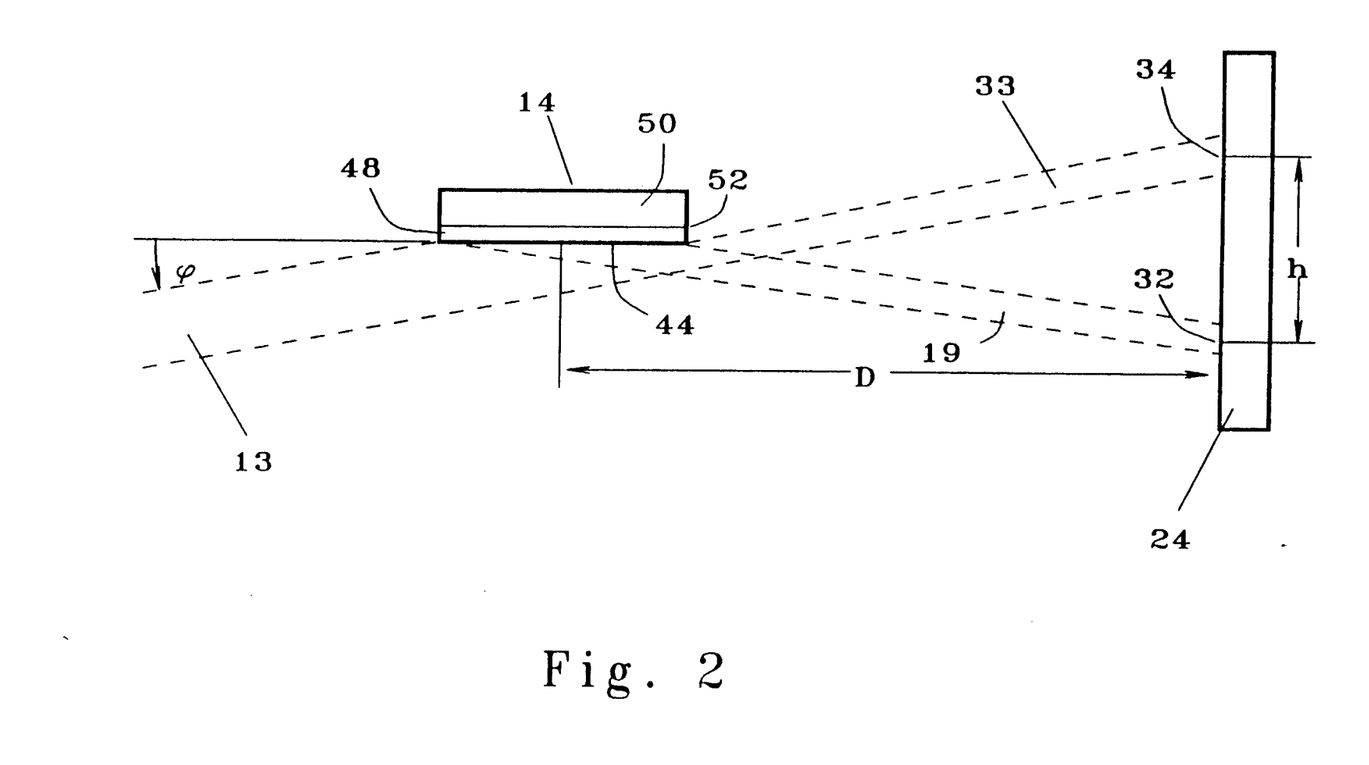
FIG. 2 shows schematically how the grazing angle of incidence can be determined from the embodiment shown in FIG. 1.

Referring now to FIG. 1, an x-ray tube 10 is a source of x-rays that pass through collimator 12 to provide a collimated x-ray beam 13 (shown in greater detail in FIG. 2). The collimated x-ray beam 13 interacts with optically polished sample 14 that is retained in vacuum chamber 15. The sample 14 is fixed on sample support 16 to be in a fixed, predetermined orientation with respect to an electron spectrometer, cylindrical mirror analyzer 18, that is used to analyze the energy of photoelectrons 21 emitted from the sample 14 when the collimated x-ray beam 13 interacts with the sample 14. Alternatively, the electron spectrometer could be a hemispherical analyzer or a 127° sector analyzer. The degree of collimation of the x-ray beam 13 is such that its angle of divergence is small compared with the critical angle of the materials being studied.

The source of x-rays may be a conventional x-ray tube 10, as shown in FIG. 1, or it may be a synchrotron radiation light source, or some other source capable of producing monochromatic x-rays with energies in the range 100 eV to 10 keV. The collimator 12 may include one or more slits (e.g. Soller slits) or parallel metal plates. Alternatively, the collimator 12 may be a crystal or crystals from which a collimated beam is obtained by diffraction.

With the apparatus of the invention, the grazing angle of incidence of the incident collimated x-ray beam 13 onto the sample 14 is changed without changing the position of the sample 14 and without altering the relationship of the sample 14 to the electron spectrometer 18. In FIG. 1 this angle is changed by using a mechanical manipulator 17. The manipulator incorporates a metal bellows 20 which allows for motion of the x-ray tube 10 10 inside the vacuum chamber 15 while preserving the vacuum. The mounting of the x-ray tube 10 and the metal bellows 20 is constrained by a circular track 22, by which means it is possible to rotate the x-ray tube 10 on a radius originating at the center of the surface of the sample 14. The rotation is accomplished by a screw adjustment 23 or other such constraint.

Further as shown in FIG. 1, a stream 21 of photoelectrons are emitted from the sample 14 and enter the cylindrical mirror analyzer 18. In addition, a reflected x-ray beam 19 (also shown in FIG. 2) falls upon an x-ray detector 24 which consists of a micro channel plate 26 used in conjunction with a phosphor screen 28. The phosphor screen 28 can be viewed from outside the vacuum chamber 15 through window 30.

As shown schematically in FIG. 2, x-ray detector 24 is an area detector. The reflected x-ray beam 19 from the sample 14 falls upon a first location 32 of the x-ray detector 24, and a portion 33 of the incident x-ray beam 13 that does not fall upon the sample 14 goes past the sample 14 and falls directly upon a second location 34 of the x-ray detector 24. The vertical distance along the x-ray detector 24 between the first location 32 and the second location 34 of the x-ray detector 24 is designated as height "h".

The grazing angle of incidence with which the x-ray beam 13 strikes the sample 14 is accurately determined using the area x-ray detector 24. In FIG. 2 the grazing angle of incidence is $\phi$. This angle can be found by the relation $\tan\phi = h/(2D)$, where "h" is the displacement between (a) the portion 33 of the collimated x-ray beam 13 that bypasses the sample 14 and (b) the reflected beam 19 as measured on the area detector; and "D" is the known distance between the center of the top surface of the sample 14 and the x-ray detector 24. More specifically, as stated above, "h" is the vertical distance along the x-ray detector 24 between the first location 32 and the second location 34 of the x-ray detector 24.

Although the x-ray detector 24 in the embodiment shown in FIG. 1 includes a micro channel plate 26 and phosphor screen 28, the detector 24 could also consist of a charge-coupled device array with appropriate sensing electronics.

Figure 3:
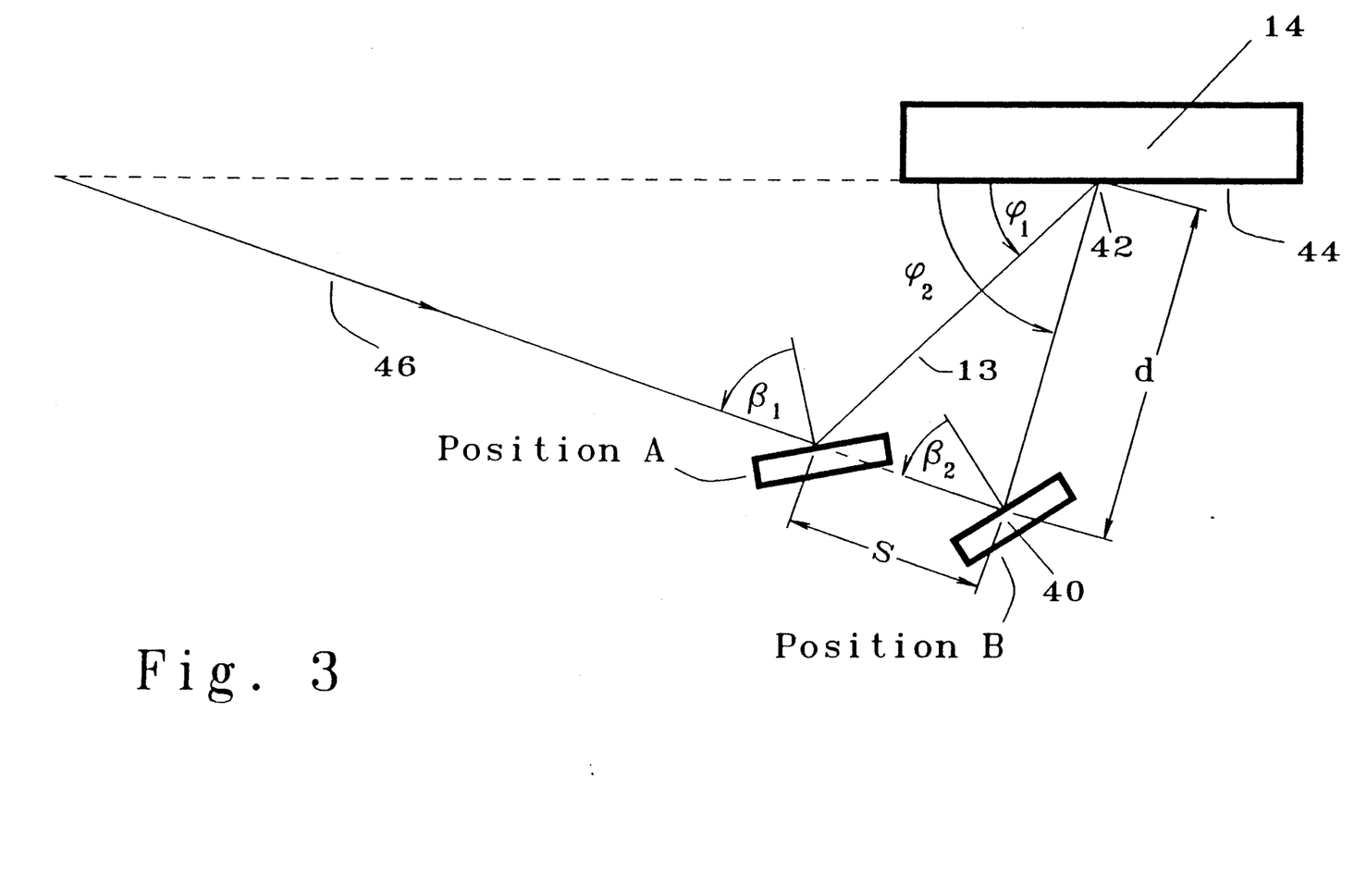
FIG. 3 shows schematically an alternative partial embodiment where the grazing angle of incidence of the collimated x-ray beam on the sample is controlled by a moving x-ray mirror.

In FIG. 3, alternate means are described for varying the grazing angle of incidence of the collimated x-ray beam 46 and the sample 14 whose orientation is fixed with respect to the cylindrical mirror analyzer 18. In FIG. 3, the grazing angle of incidence $\phi$ is varied by an x-ray mirror 40 which uses the principle of total external reflection over a range of angles which are less than the critical angle. The x-ray mirror 40 in FIG. 3 reflects the collimated x-ray beam 46 onto the sample 14. The mirror 40 is mounted on a mechanism which translates and rotates it. The translation and rotation are such that the collimated x-ray beam 46 is incident about a central point 42 on the top surface 44 of the sample 14. This can be accomplished by ensuring that:

$$S = 2d \tan[(\phi_2 - \phi_1)/2]$$

$$\beta_1 - \beta_2 = \tfrac{1}{2}(\phi_2 - \phi_1)$$

in the embodiment of the mechanism for manipulation where "S" is a distance along a central track to the axis of the mirror 40; "$\beta$" is an angle between the x-ray beam 46 incident on the mirror 40 and its surface normal; and "d" is the distance between the rotation axis of the mirror 40 and the center 42 of the sample 14. More specifically, "$\beta_1$" is the angle between the x-ray beam 46 incident on the mirror 40 in position A and its surface normal in FIG. 3; and "$\beta_2$" is the angle between the x-ray beam 46 incident on the mirror 40 in position B and its surface normal in FIG. 3.

Preferably, the top surface 44 of the sample 14 is optically flat. This is to ensure: 1) that as the grazing angle which the collimated x-ray beam makes with the sample surface becomes small, all parts of the surface have the same grazing angle of incidence with the beam, and 2) that the sample surface is capable of optically reflecting the x-rays. Similarly, in the case of a surface which is covered with an overlying layer 1) the interface of the substrate with the overlying layer should be optically flat; and 2) the surface of the overlayer should also be optically flat.

With the invention, as the grazing angle $\phi$, which the collimated x-ray beam 13 makes with the surface of sample 14, becomes smaller than a critical angle $\phi_c$, the electric field is enhanced in the surface region so that there is enhanced photoelectron emission from the surface layer. This property is discussed in an article by B. L. Henke, Physical Review A, vol. 6, P. 92–104 (1972).

More specifically, in the case where the sample contains a top layer or overlayer 48 which has a different index of refraction than an underlying substrate 50, as shown in FIG. 2, then the overlayer 48 will also have a different critical angle than the substrate 50. In this case, the teachings of the above-cited Henke article are not sufficient to describe the intensity of x-ray fields at various depths inside the overlayer 48 and at the interface 52 with the substrate 50, since the reflection of the x-rays at the surface 44 of the sample 14 and at the interface 52 and their interference must be taken into account but are not taken into account by the Henke article.

The case of the reflection of x-rays from a multilayered material is discussed by L. G. Parratt, Physical Review, Vol. 95, No. 2, pp. 359–369 (1954). However, Parrat does not calculate the distribution of strength of the x-ray electric field responsible for photoemission within a layer.

The values of the x-ray electric field at all depths in each film and in the substrate may be calculated by considering the matching of boundary conditions for the electromagnetic waves propagating into and out of the interface between each layer, taking into account the index of refraction and the x-ray absorption coefficient in each layer. A constructive interference will occur between the electric field of the wave propagating into the material and the wave originating from reflection at an interface under conditions of total internal reflection satisfied at interface 48 between two layers. It will result in a total field which is stronger at the interface than the field at the surface. This is because the field which is due to the reflection is attenuated on the way out of the material and because the reflected wave is at a maximum of field strength at the interface for angles of incidence near the critical angle.

The photoelectron emission which is observed is proportional to the intensity of the electric field at each point in the layer, and the total photoemission intensity is proportional to the integrated intensity of the electric field throughout each layer.

The critical angle is defined as $\phi_c = (\chi_o)^{\frac{1}{2}}$, where $\chi_o$, the dielectric susceptibility, is related to the index of refraction. Generally, $\chi_o$ is determined by the product of the atomic form factor (the number of electrons capable of responding to the x-ray field) of the elements involved, and the number of such atoms packed into a unit volume of the sample. For a given energy of the x-rays, the critical angle is generally smaller when the product of the form factor and the number density is low and larger when the product of the form factor and the number density is high.

For the cases of interest which have been mentioned above, it is desirable that the critical angle for total external reflection from the overlayer 48 be smaller than the critical angle for total external reflection from the substrate 50. Then an angle of incidence which lies between the two critical angles will permit the x-ray beam to penetrate the overlayer 48 but be reflected by the substrate 50.

Examples which would satisfy such a condition at some x-ray energy would be nickel oxide as an overlayer on nickel metal and aluminum as an overlayer on the semiconductor germanium. In general, a wide variety of cases of overlayers and substrates exist where the condition is satisfied. In the case of nickel oxide as an overlayer on nickel metal, a calculation using x-rays at an energy of the aluminum K$\alpha$ x-ray line (1486.7 eV) would give a critical angle $\phi_c = 1.97$ for nickel oxide and $\phi_c = 2.24°$ for nickel metal, thus satisfying the condition.

In accordance with the method of the invention, it is possible to enhance the x-ray intensity at the interface 52 between the materials when the x-rays have a grazing angle of incidence which is less than or equal to the critical angle of the substrate 50, but greater than the critical angle of the top layer 48. Under these circumstances, there is very little reflection of x-rays from the surface 44 of the overlayer, but a considerable reflection of x-rays from the interface 52 between the overlayer 48 and the substrate 50. Due to the constructive addition between the incident and reflected x-ray electric fields at the interface 52, the field intensity at the interface and just above it will be enhanced relative to the surface, and the photoelectron emission will also be enhanced.

Figure 4:
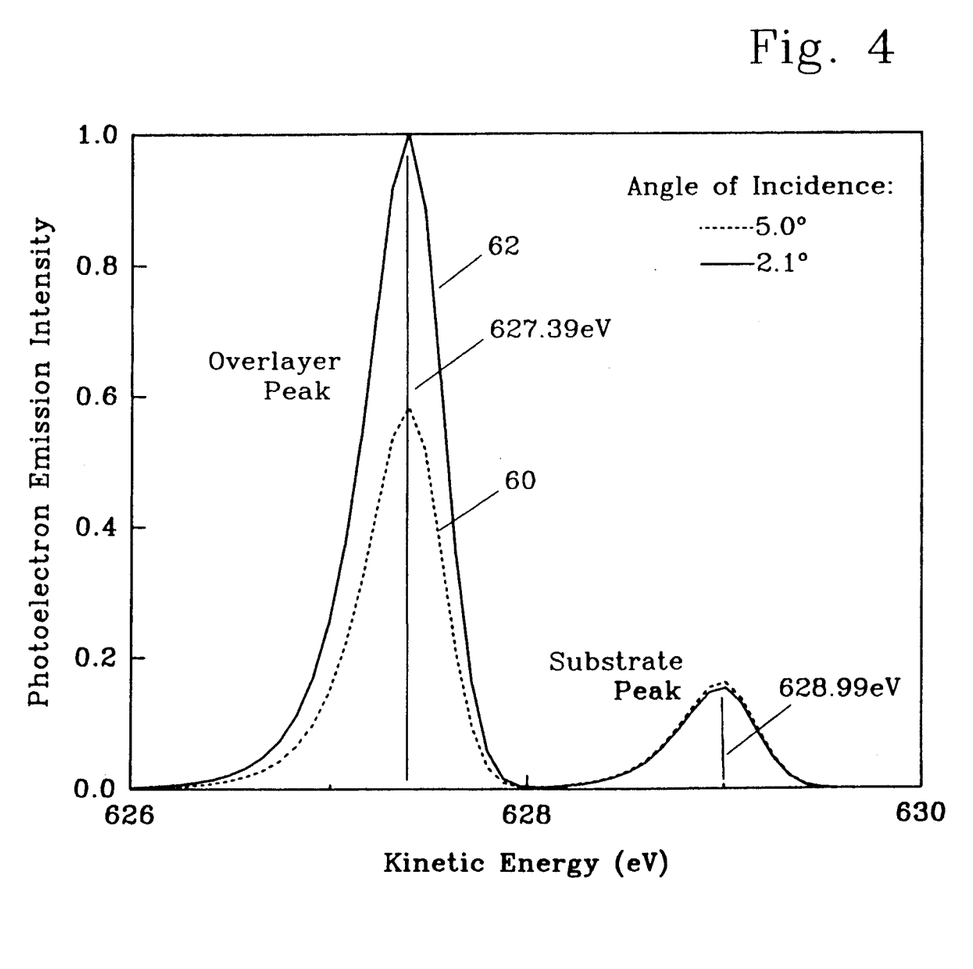
FIG. 4 shows the effect of varying the grazing incidence angle of a collimated x-ray beam on a sample having a top layer of nickel oxide and a substrate layer of nickel, whereby by decreasing the grazing angle of incidence from 5 degrees to 2.1 degrees, the signal from the nickel oxide at the nickel oxide/nickel interface relative to the signal from the nickel is increased due to the total reflection of x-ray at the interface and the subsequent constructive interference of the incident and reflected wave fields.
Figure 5:
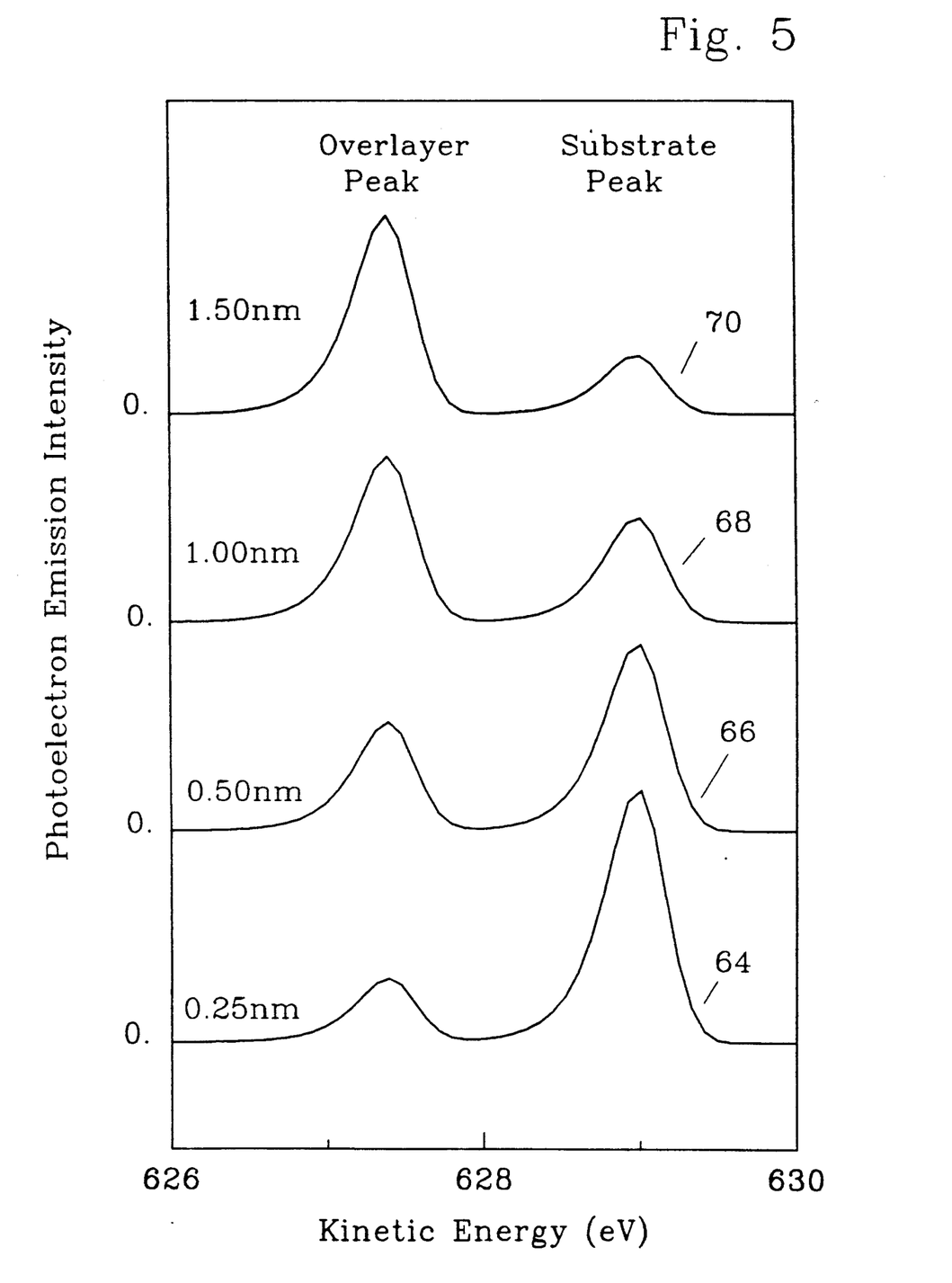
FIG. 5 shows the variation in the respective spectral peaks due to the overlayer and the substrate for overlayers of 0.25 nm, 0.50 nm, 1.00 nm, and 1.50 nm, of nickel oxide on nickel at a fixed angle of incidence of 2.1° respectively.
Figure 6:
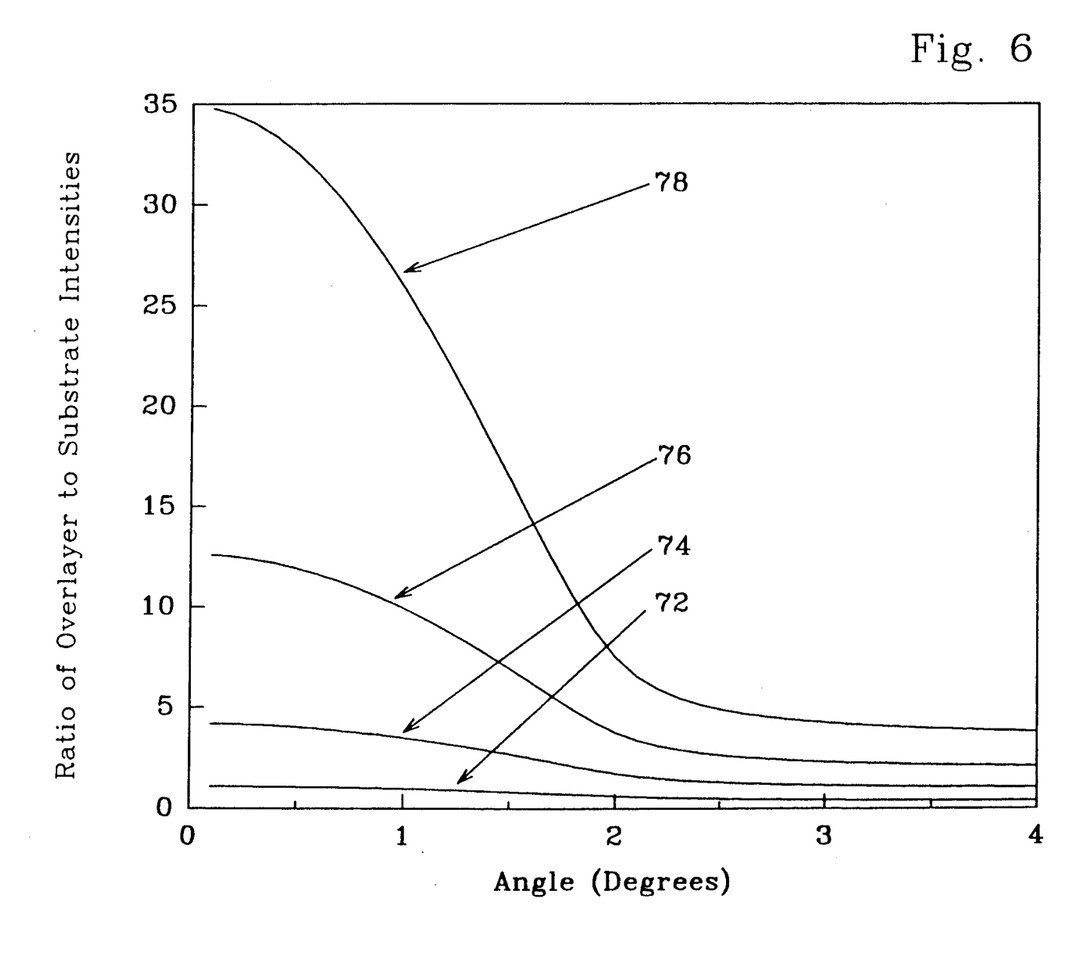
FIG. 6 shows the variation in the ratio of the peak intensity due to photoelectron emission from the surface layer to that coming from the substrate as the angle of incidence is varied.

The method of the invention for analyzing a multilayer sample and for determining the depth of a top layer is illustrated in FIGS. 4, 5, and 6. It is recalled that for a two-layer sample, the method of the invention includes the following steps. The sample is supported in a evacuated chamber with a predetermined, fixed orientation with respect to an electron detector. A collimated x-ray beam is directed to the sample at a specified grazing angle with respect to the sample. The grazing angle of the collimated x-ray beam is monitored by detecting x-rays reflected off of the sample with an x-ray detector, and data are generated which represent the grazing angle. The grazing angle is controlled with respect to the sample such that the grazing angle is at an angle greater than the first-layer critical angle and less than the second-layer critical angle. Photoelectron emission from the sample is detected with the energy analyzing electron detector, and data are generated which represent an energy distribution of the detected photoelectron emission. The data representing the photoelectron energy distribution are evaluated to determine the intensity of peaks corresponding to photoelectron emission from the chemical species in the first and second layers. The ratio of the intensities of the two peaks may be used to determine the thickness of layer one.

Turning to FIG. 4, calculated differences between the photoelectron emission spectrum of an overlayer and the photoelectron emission spectrum of a substrate are shown. More specifically, the sample includes a semiconductor substrate of nickel metal and an overlayer of the oxide of nickel. The overlayer of the nickel oxide is 2.0 nm thick. The x-rays used had an energy of 1486.7 eV as obtained from an x-ray tube with an aluminum target. The respective critical angles of the oxide of nickel and the nickel substrate are both less than 5 degrees. However, the critical angle of the oxide of nickel is less than 2.1 degrees, whereas the critical angle of the nickel substrate is greater than 2.1 degrees. The calculation has been carried out by consistently matching the boundary conditions of the x-ray fields at the surface of the overlayer and at the interface between the overlayer and the substrate. The total integrated intensity of photoelectrons which are capable of escaping from the overlayer (overlayer peak) and the substrate (substrate peak) are each depicted as separate peaks. The peaks shown in FIG. 4 correspond to chemically shifted photoemission peaks from the nickel atoms in the environment of the oxide and nickel atoms in the environment of a pure nickel substrate.

In FIG. 4, the curve 60 depicted as a dashed line corresponds to the photoelectron spectrum of the sample interacting with the collimated x-ray beam at the relatively large grazing angle of 5 degrees. On the other hand, the curve 62 depicted as a continuous line corresponds to the photoelectron spectrum of the sample interacting with the collimated x-ray beam at the relatively small incidence angle of 2.1 degrees in accordance with the invention.

It is noted that for curve 60, the overlayer peak (at a first characteristic electron energy line at about 627.4 eV) has a photoelectron emission intensity of about 0.58 photoelectron intensity units and the substrate peak has a photoelectron emission intensity of about 0.16 photoelectron intensity units (at a second characteristic electron energy line at about 629.0 eV).

On the other hand, for curve 62, the overlayer peak (also at the first characteristic electron energy line at about 627.4 eV) has a higher photoelectron emission intensity (about 1.0 photoelectron emission intensity units) and the photoelectron emission intensity of the substrate peak (also at the second characteristic electron energy line at about 629.0 eV) is reduced to about 0.15 photoelectron emission intensity units.

Generally, the variation in the amplitudes of the respective photoemission peaks of the two species (oxide of nickel overlayer layer and nickel substrate) as the angle of incidence $\phi$ is changed from an angle greater than the critical angle of both the overlayer and the substrate, to an angle less than the critical angle of the substrate but greater than the critical angle of the overlayer illustrates the enhancement of photoelectron emission which the method of the invention would give to the overlayer atoms lying in proximity to the interface with the substrate.

The variation in the amplitudes of photoemission intensity peaks for a particular characteristic electron energy line with grazing incidence angle can be used to determine overlayer thickness in some systems. The index of refraction for the overlayer is often quite different from, and less than, that of the substrate. When this is the case, the variation in the photoelectron yield with incident angle will be influenced by the thickness of the overlayer. For some cases, it is possible to deduce this thickness by comparison of the photoemission line intensities on a measured curve in comparison with the calculated curve.

Turning to FIG. 5, for a constant grazing angle of incidence of 2.1 degrees, a series of calculated curves show the effect of oxide thickness on the photoemission energy yield are shown. Curve 64 depicts a calculated photoelectron emission spectrum for a layer of nickel oxide that is 0.25 nm thick on a substrate of nickel. Curve 66 depicts a calculated photoelectron emission spectrum for a layer of nickel oxide that is 0.50 nm thick on a substrate of nickel. Curve 68 depicts a calculated photoelectron emission spectrum for a layer of nickel oxide that is 1.00 nm thick on a substrate of nickel. Curve 70 depicts a calculated photoelectron emission spectrum for a layer of nickel oxide that is 1.50 nm thick on a substrate of nickel in each of the curves 64, 66, 68, and 70 in FIG. 5, the left peak is due to the layer of the oxide of nickel and the right peak is due to the nickel substrate.

The curves in FIG. 5 are obtained by using the teachings in the Henke et al article mentioned herein above and by going beyond the Henke et al article by further taking into account (a) the reflection of the x-rays at the surface 44 of the sample 14 (b) the reflection of the x-rays at the interface 52, (c) the constructive interference caused by the addition of the electric field of the incident x-ray wave propagating inside the overlayer and the electric field of the reflected x-ray wave propagating out, (d) the attenuation of photoelectrons emitted by the incident wave in the substrate as they escape through the overlayer, and (e) the attenuation of the photoelectrons emitted in the overlayer as they escape. The method of calculation of the electric fields is that which was described earlier.

The method of calculation can in fact be applied to any angle as is shown in FIG. 6. Curve 72 shows the ratio of th overlayer peak height to the substrate peak height calculated over a range of angles instead of for a single angle for an overlayer thickness of 0.5 nm. Curve 74 shows the same ratio for an overlayer thickness of 1.0 nm. Curve 76 shows the same ratio for an overlayer thickness of 1.5 nm. Curve 78 shows the same ratio for an overlayer thickness of 2.0 nm. A measurement of the overlayer thickness of an actual sample can be made by obtaining the ratios of the heights of the photoemission peaks from the overlayer and the substrate for a series of incidence angles and comparing them to the calculated ratios shown in FIG. 6. The calculated curves in FIG. 6 would serve as standards against which the actual sample would be compared.

Alternatively, a series of known standards having known thicknesses of oxide layers or other thin films on known substrates can be prepared. Then the photoelectron emission of an unknown sample would be compared to the known standards.

There are a number of reasons why the method of the invention, employing a grazing angle of x-ray incidence has advantages over prior art methods employing measurement of photoelectron emission using a large angle of x-ray incidence. In comparing photoelectron emission for a large takeoff angle versus photoelectron emission for a grazing takeoff angle, the former electrons can escape atoms at a greater depth beneath the surface, while the latter electrons must come from atoms near the surface owing to the greater amount of matter which they must otherwise penetrate in order to escape. In both cases the depth which is sampled is limited by the quantity of matter which the electrons must traverse in order to escape, and there is always an attendant energy distortion to the spectral line due to inelastic collisions in making their way out of the sample.

Figure 7:
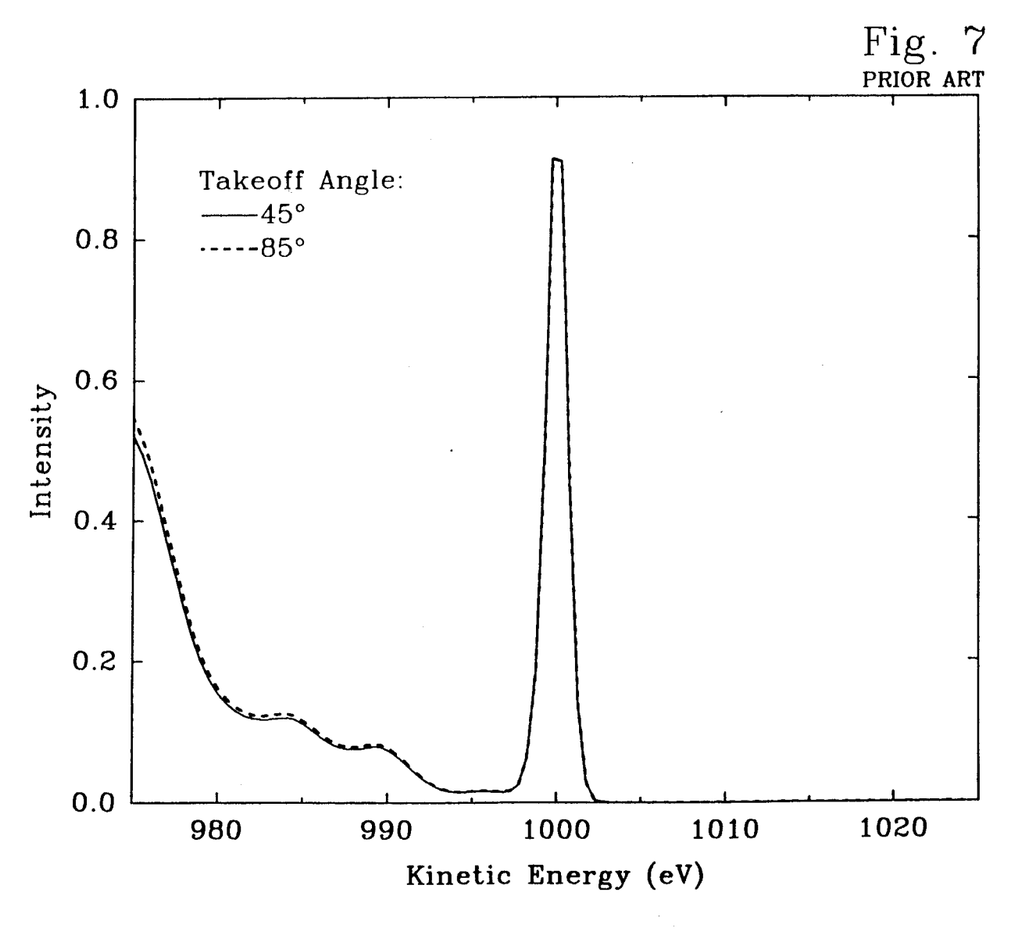
FIG. 7 shows large distortions of the spectral lineshape of photoelectron emission when using a prior art technique of varying the takeoff angle of x-rays that interact with a sample.

In FIG. 7 a calculated curve provides a comparison of the photoelectron energy spectra where x-ray penetration depth is limited by means of prior art near normal (85 degrees) and large, but reduced, takeoff angles (45 degrees) which result from changing the angle of the sample with respect to the electron spectrometer. The x-ray photoemission spectrum is calculated for photoelectrons limited to near normal and reduced takeoff angles from the metal tungsten, using as a source the characteristic radiation of 1253.6 eV from an x-ray tube with a magnesium target. The method of calculation is that described by S. Tougaard in Surface and Interface Analysis, vol. 11, p .453–472, (1988). The calculated photoemission lines are normalized to the same height for the purposes of comparison. In both cases the spectral lineshape shows a distribution of photoelectrons at lower kinetic energy (from about 975 ev to 993 ev) than the main peak (at approximately 1,000 eV) due to inelastic scattering as the photoelectrons escape from the surface. Such photoelectrons that have a lower kinetic energy than the main peak would cause significant distortion of a separate peak due to an overlayer.

An additional distortion in the photoemission lines has been documented when carrying out a process of rotating the sample with respect to an x-ray source and an electron spectrometer whose orientation are held constant with respect to each other, as is conventionally the case. See N. E. Erickson and C. J. Powell, Journal of Vacuum Science & Technology A4, 1551–1556 (1986). This distortion is due to the change in sample position relative to the focal point of the electron spectrometer.

Figure 8:
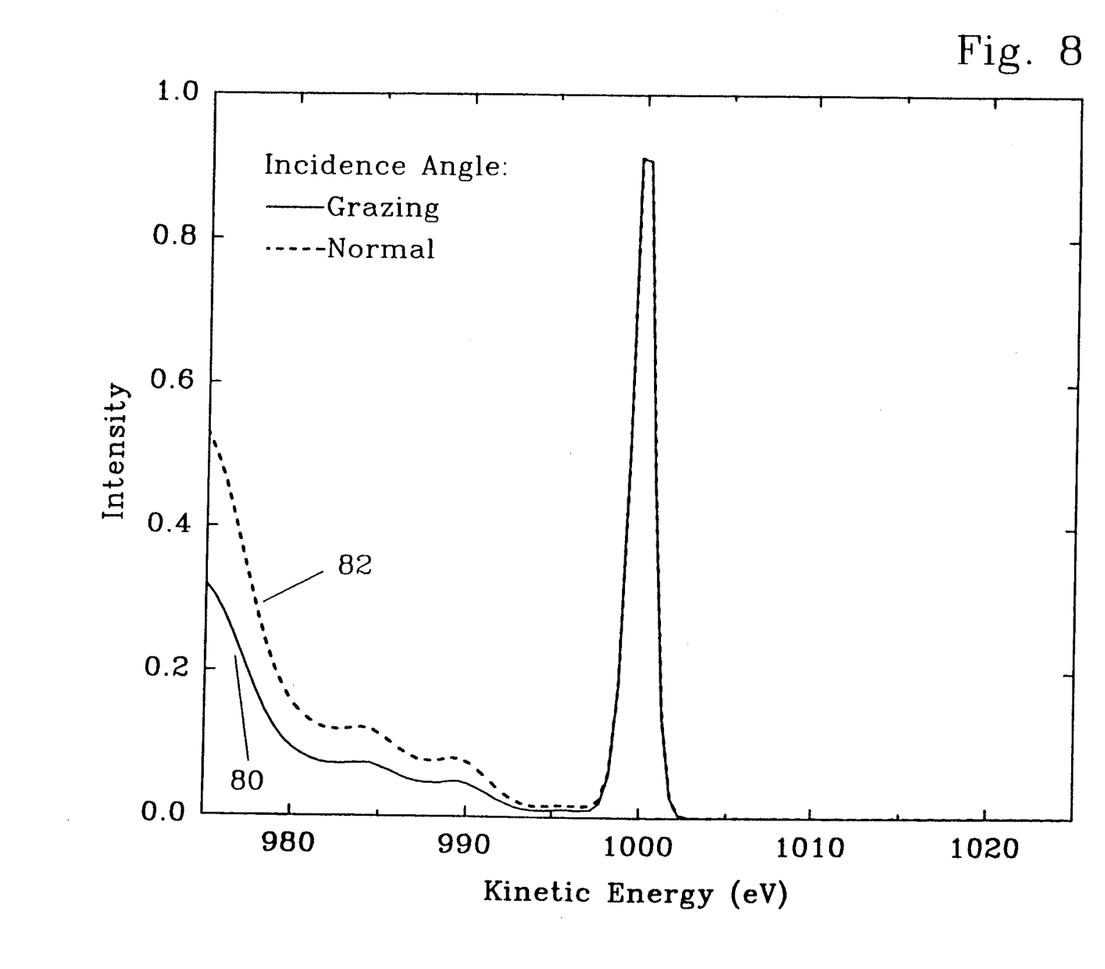
FIG. 8 shows significantly reduced distortions of the spectral lineshape of photoelectron emission realized by the system of the invention using a small grazing angle of incidence of x-rays from a collimated x-ray beam that interacts with a sample whose orientation with respect to an electron analyzer is fixed.

The above-mentioned distortions in photoelectron emission are greatly reduced by employing the apparatus and method of the invention. Evidence for the reduced lineshape distortion that results from using the invention is provided by FIG. 8 in which a comparison is easily made between calculated photoelectron energy spectra where penetration depth is limited by means of x-ray incidence angles above and below the critical angle at the surface of the sample. In FIG. 8, the x-ray photoemission spectra are calculated for the system in which the sample is held fixed with respect to the electron spectrometer; and depth variation, obtained by varying the angle of incidence of the collimated x-ray beam from normal incidence to just below the critical angle as described, is provided with the invention. It is seen that the distortion of the photoemission lines for a small grazing angle of incidence in FIG. 7 is considerably reduced (see curve 80) compared to a normal angle of incidence (see curve 82). The reduced distortion with the grazing angle of incidence is due to the fact that the penetration depth is limited partially by the x-ray penetration depth rather than totally by the escape depth of the photoelectrons.

Thus it can be seen that by employing the principles of the invention, measuring the depth distribution in a multilayer sample does not suffer the disadvantages of prior art methods. More specifically, by using the principles of the invention, energy distortion which has been documented due to change in the relative motion of the sample with respect to the spectrometer is eliminated. Furthermore, energy distortion due to a large angle of incidence is considerably reduced with the invention.

Moreover, with the invention, for photoemission lines in which the changes due to chemical environment are small and must be distinguished by means of fitting peaks with the variation of binding energy, the diminished distortion provided by employing the principles of the invention provides a distinct advantage.

What is claimed is:

1. An x-ray photoelectron emission analyzer apparatus for analyzing a sample in an evacuated chamber, the apparatus comprising:

an x-ray source;

collimating means for collimating x-rays from the source for providing a collimated x-ray beam which interacts with the sample within the evacuated chamber;

incidence angle adjustment means for adjusting the collimated x-ray beam for permitting the collimated x-ray beam to interact with the sample with an adjustable grazing incidence angle;

electron detector means, maintained in a predetermined, fixed orientation with respect to the sample, for detecting photoelectron emission from the sample;

fixed sample support means for maintaining the sample in the evacuated chamber in a predetermined, fixed orientation with respect to said electron detector means; and means for monitoring the grazing incidence angle of the collimated x-ray beam that interacts with the sample.

2. The apparatus described in claim 1 wherein said x-ray source includes an x-ray tube.

3. The apparatus described in claim 1 wherein said x-ray source includes a synchrotron light source which provides monochromatized x-rays.

4. The apparatus described in claim 1 wherein said collimating means includes one or more slits.

5. The apparatus described in claim 1 wherein said collimating means includes parallel plates.

6. The apparatus described in claim 1 wherein said collimating means includes one or more x-ray diffraction crystals.

7. The apparatus described in claim 1 wherein said electron detector means includes means for determining kinetic energy of electrons photoemitted from the sample.

8. The apparatus described in claim 1 wherein said electron detector means includes means for determining the number of electrons of a specified kinetic energy photoemitted by the sample.

9. The apparatus described in claim 1 wherein said electron detector means includes a cylindrical mirror electron analyzer.

10. The apparatus described in claim 1 wherein said electron detector means includes a hemispherical electron analyzer.

11. The apparatus described in claim 1 wherein said electron detector means includes a 127° sector electron analyzer.

12. The apparatus described in claim 1 wherein said incidence angle adjustment means includes means by which the angle of incidence of the collimated x-ray beam can be changed without changing the point of illumination on the sample or the distance between the x-ray source and the sample.

13. The apparatus described in claim 1 wherein said incidence angle adjustment means includes a circular track along which the said x-ray source is moved.

14. The apparatus described in claim 1 wherein said incidence angle adjustment means includes an adjustable x-ray mirror located between said x-ray source and the sample.

15. The apparatus described in claim 1 wherein said grazing angle monitoring means includes means for detecting x-rays reflected off of the sample.

16. The apparatus described in claim 1 wherein said grazing angle monitoring means includes means for detecting the exit angle of x-ray reflected off of the sample.

17. The apparatus described in claim 1 wherein said grazing angle monitoring means includes a micro channel plate.

18. The apparatus described in claim 1 wherein said grazing angle monitoring means includes a charge-coupled device array.

19. The apparatus described in claim 1 wherein the sample is an optically polished sample.

20. An x-ray photoelectron emission analyzer apparatus for analyzing a sample in an evacuated chamber, the apparatus comprising:
- an x-ray source;
- collimating means for collimating x-rays from the source for providing a collimated x-ray beam which interacts with the sample within the evacuated chamber, wherein the sample includes an optically polished top layer;
- grazing incidence angle adjustment means for adjusting the collimated x-ray beam for permitting the collimated x-ray beam to interact with the sample with an adjustable grazing incidence angle;
- electron detector means, maintained in a predetermined, fixed orientation with respect to the sample, for detecting photoelectron emission from the sample, wherein said electron detector means includes an electron energy analyzer and means for providing a record of the quantity and kinetic energies of electrons photoemitted from the sample;
- fixed sample support means for maintaining the sample in the evacuated chamber in a predetermined, fixed orientation with respect to said electron detector means; and
- means for monitoring the grazing incidence angle of the collimated x-ray beam that interacts with the sample, wherein said grazing incidence angle monitoring means includes means for detecting x-rays reflected off of the sample.

21. A method for analyzing a multilayer sample having a first layer and a second layer, wherein the first layer is a top layer and has a first-layer critical angle, and wherein the second layer has a second-layer critical angle, the method comprising the steps of:
- supporting the sample in a evacuated chamber with a predetermined, fixed orientation with respect to an electron detector;
- directing a collimated x-ray beam to the sample at a grazing incidence angle with respect to the sample;
- monitoring a grazing exit angle of the collimated x-ray beam with respect to the sample by detecting x-rays reflected off of the sample with an x-ray detector and generating data representing the grazing angle;
- controlling the incidence angle with respect to the sample such that the incidence angle is set to one or more incidence angles between the first-layer critical angle and the second layer critical angle;
- detecting photoelectron emission from the sample with the electron detector and generating data representing an energy distribution of the detected photoelectron emission for the one or more incidence angles;
- evaluating the data, for the one or more incidence angles, representing the energy distribution of the detected photoelectron emission to determine peaks in intensity of photoemission at specific energies corresponding to different chemical species and
- determining thickness of the first layer based on the intensity of photoelectron emission peaks corresponding to the chemical species of the first and second layers at the one or more incidence angles.

22. The method described in claim 21 wherein the grazing angle of incidence is at an angle greater than the first-layer critical angle and less than the second-layer critical angle to enhance the photoelectron emission intensity from the top layer.

23. The method described in claim 21 wherein the sample has an optically polished first layer.

24. The method described in claim 21 wherein the sample includes a first layer of nickel oxide and a second layer of nickel.

25. The method described in claim 21 wherein the sample includes a first layer of a metal oxide and a second layer of a metal.

26. The method described in claim 21 wherein the grazing incidence angle is in a range of 0.1 to 10 degrees.

27. The method described in claim 21 wherein:

the sample includes a third layer that underlies the second layer;

the third layer has a third-layer critical angle;

the grazing incidence angle is at an angle greater than the second-layer critical angle and less than the third-layer critical angle, whereby photoelectron emission intensity from the second layer is enhanced; and determining thickness of the second layer based on the intensity of photoemission peaks corresponding to the chemical species of the second and third layers.

28. The method described in claim 21 wherein:

the sample includes an "n"th layer that underlies an "n-1"th layer;

the "n"th layer has an "n"th-layer critical angle;

the "n-1"th layer has an "n-1"th critical angle;

the grazing angle is at an angle greater than the "n-1"th-layer critical angle and less than the "n"th-layer critical angle, whereby photoelectron emission intensity from the "n-1"th layer is enhanced; and determining thickness of the "n-1"th layer based on the intensity of photoemission peaks corresponding to the chemical species of the "n-1"and "n"th layers.

29. The method described in claim 21 wherein the collimated x-ray beam has an energy range from 100 to 10,000 electron volts.

30. The method described in claim 21, further including the step of:

determining an interface between the first layer and the second layer by detecting a total x-ray field, at the interface, which is stronger than an x-ray field at a layer surface, for angles of incidence that are less than or equal to the second layer critical angle and greater than the first-layer critical angle.

31. A method for analyzing a multilayer sample having a first layer and a second layer, wherein the first layer is a top layer and has a first-layer critical angle, and wherein the second layer has a second-layer critical angle, the method comprising the steps of:

supporting the sample in a evacuated chamber with a predetermined, fixed orientation with respect to an electron detector, wherein the sample is a semiconductor and has an optically polished first layer;

directing a collimated x-ray beam to the sample at a grazing incidence angle with respect to the sample;

monitoring the grazing incidence angle of the collimated x-ray beam with respect to the sample by detecting x-rays reflected off of the sample with an x-ray detector and generating data representing the grazing incidence angle;

controlling the grazing incidence angle with respect to the sample such that the incidence angle includes angles greater than the first-layer critical angle and less than the second layer critical angle;

detecting photoelectron emission from the sample with the electron detector and generating data representing the quantity of electrons at each kinetic energy;

evaluating the data representing the energy distribution of the detected photoelectron emission to determine peaks in intensity corresponding to photoemission from different chemical species; and determining thickness of the first layer based on comparing the intensity of peaks due to photoemission from the different chemical species at different incidence angles.

32. A method for analyzing a sample, comprising the steps of:

supporting the sample in a evacuated chamber with a predetermined, fixed orientation with respect to an electron detector;

directing a collimated x-ray beam at a grazing incidence angle with respect to the sample;

monitoring a grazing exit angle of the collimated x-ray beam with respect to the sample by detecting x-rays reflected off of the sample with an x-ray detector:

controlling the grazing incidence angle of the collimated x-ray beam with respect to the sample based on the monitored grazing exit angle of the x-rays reflected off of the sample;

detecting photoelectron emission from the sample with the electron detector; and evaluating the detected photoelectron emission to determine different chemical species in the sample.

* * * * *